United States Patent [19]

Michel

[11] Patent Number: 5,509,905
[45] Date of Patent: Apr. 23, 1996

[54] INJECTOR DISPLAY

[75] Inventor: Peter Michel, Burgdorf, Switzerland

[73] Assignee: Medimpex Ets, Liechtenstein

[21] Appl. No.: 133,125

[22] PCT Filed: Feb. 12, 1993

[86] PCT No.: PCT/CH93/00038

§ 371 Date: Oct. 13, 1993

§ 102(e) Date: Oct. 13, 1993

[87] PCT Pub. No.: WO93/16743

PCT Pub. Date: Sep. 2, 1993

[30] Foreign Application Priority Data

Feb. 24, 1992 [CH] Switzerland ............... 00555/92

[51] Int. Cl.⁶ ............................................. A61M 5/00
[52] U.S. Cl. ................................................ 604/207
[58] Field of Search ............... 604/207–211, 30–34, 604/51, 52, 67, 246–249; 128/DIG. 1, DIG. 13

[56] References Cited

U.S. PATENT DOCUMENTS

| | | | |
|---|---|---|---|
| 4,959,056 | 9/1990 | Dombrowski et al. | 604/211 |
| 5,092,842 | 3/1992 | Bechtold et al. | 604/211 |
| 5,180,371 | 1/1993 | Spinello | 604/207 |
| 5,236,416 | 8/1993 | McDaniel et al. | 128/DIG. 1 |
| 5,244,465 | 9/1993 | Michel | 604/208 |
| 5,295,976 | 3/1994 | Harris | 604/211 |
| 5,300,042 | 4/1994 | Kosgoff et al. | 604/210 |
| 5,304,152 | 4/1994 | Sams | 604/211 |
| 5,308,340 | 5/1994 | Harris | 604/208 |
| 5,370,629 | 12/1994 | Michel et al. | 604/207 |
| 5,383,865 | 1/1995 | Michel | 604/208 |

FOREIGN PATENT DOCUMENTS

| | | |
|---|---|---|
| 293958 | 12/1988 | European Pat. Off. . |
| 87/02895 | 5/1987 | WIPO . |
| 90/09202 | 8/1990 | WIPO . |

*Primary Examiner*—C. Fred Rosenbaum
*Assistant Examiner*—Manuel Mendez
*Attorney, Agent, or Firm*—Walter C. Farley

[57] ABSTRACT

The invention concerns a display for a medical injection device (1) wherein an injection dose is pre-selected by rotating an operating head (2) and then is administered by axially displacing said head. Switching devices (7, 8) are apposed to the operating head (2) to actuate switches (7, 8) of which the switch positions are transmitted to a printed circuit board (13). The printed circuit board (13) preferably contains a processor, so that values such as set injection dose, the sum of administered injection doses etc. and signals concerning operational states are shown on a display system (15).

11 Claims, 3 Drawing Sheets

INJECTOR DISPLAY

FIELD OF THE INVENTION

The invention relates to a medical-injection display for an injection device used to inject selectable doses of liquid from an ampoule or the like.

BACKGROUND OF THE INVENTION

Injection devices (hereafter called merely "devices") are used in medicine to inject liquids for instance into the human body. The present application relates to devices constructed so that patients are able to administer to themselves the injections at any time. Significant criteria are the compactness of the device which must be carried on one's person, the possibility to carry out several injections using one ampoule in the device, and accurately preselected injection doses, as well as reliability and simple handling of the device.

Such devices are known. European patent document B10 293 958 describes one employing ampoules with plungers. The plunger is advanced by a rod driven by an electric motor and the injection liquid in the ampoule is thereby expelled from the ampoule and through a needle. A sensor measures the dose-setting adjustment of the rod and hence of the plunger. The electrical signal magnitude measured is compared at a comparator with an electrical reference value previously set by the patient and can be displayed. When the dose set by the reference value has been reached, an electric check is performed each time to see whether the set dose is still present in the ampoule. If not, the electrical motor is locked up to preclude injection and this state is then displayed.

While this device can be carried on one's person, it is fairly bulky because of the electric motor and the gear sets. Also, the sensor provides an analog output and if there were a change in amplification, the desired rod adjustment conforming to the reference value might differ from the actually set value and the patient would inject the wrong dose. The patient lacks checking means. Moreover, the battery condition is not displayed, and it might be at such a Level, previous to a required injection, adequate still to control the device and feed the displays but insufficient to lower the motor and therefore the injection could not be carried out. The complexity of the electronic control of this device includes further functions not cited herein and therefore it is comparatively large.

A further device is known from WO 87/02895. It is actuated solely manually and has the bulk of a fountain pen with clip; in other words, it is easily carried on the patient's person. The injection dose can be set at a rod by rotating an operating head; this rod moreover does not touch the ampoule which is used in this device and which is filled with the injection liquid. When the operating head is displaced axially, the rod is made to touch the plunger and the adjusted dose is then expelled through a needle by said plunger. Thereupon the rod and operating head snap back and the next dose can then be set by rotating said operating head. The size of the dose is determined by the number of revolutions undergone by the operating head and illustratively may be detected by acoustic signals emitted every quarter turn.

The set dose can be checked acoustically only during setting, but not later. This constitutes to a substantial drawback because erroneous doses cannot be ruled out.

SUMMARY OF THE INVENTION

An object of the invention is to alleviate the shortcomings of both devices. To that end, it provides a display for an injection device whereby the patient is able to check reliably and subsequently the set dose and is provided information how much injection liquid remains for further injections.

BRIEF DESCRIPTION OF THE DRAWINGS

The display of the invention is elucidated below in with reference to the following drawings wherein.

The same components are referenced by the same numerals in said Figures.

DESCRIPTION OF THE PREFERRED EMBODIMENTS

Figure 1:
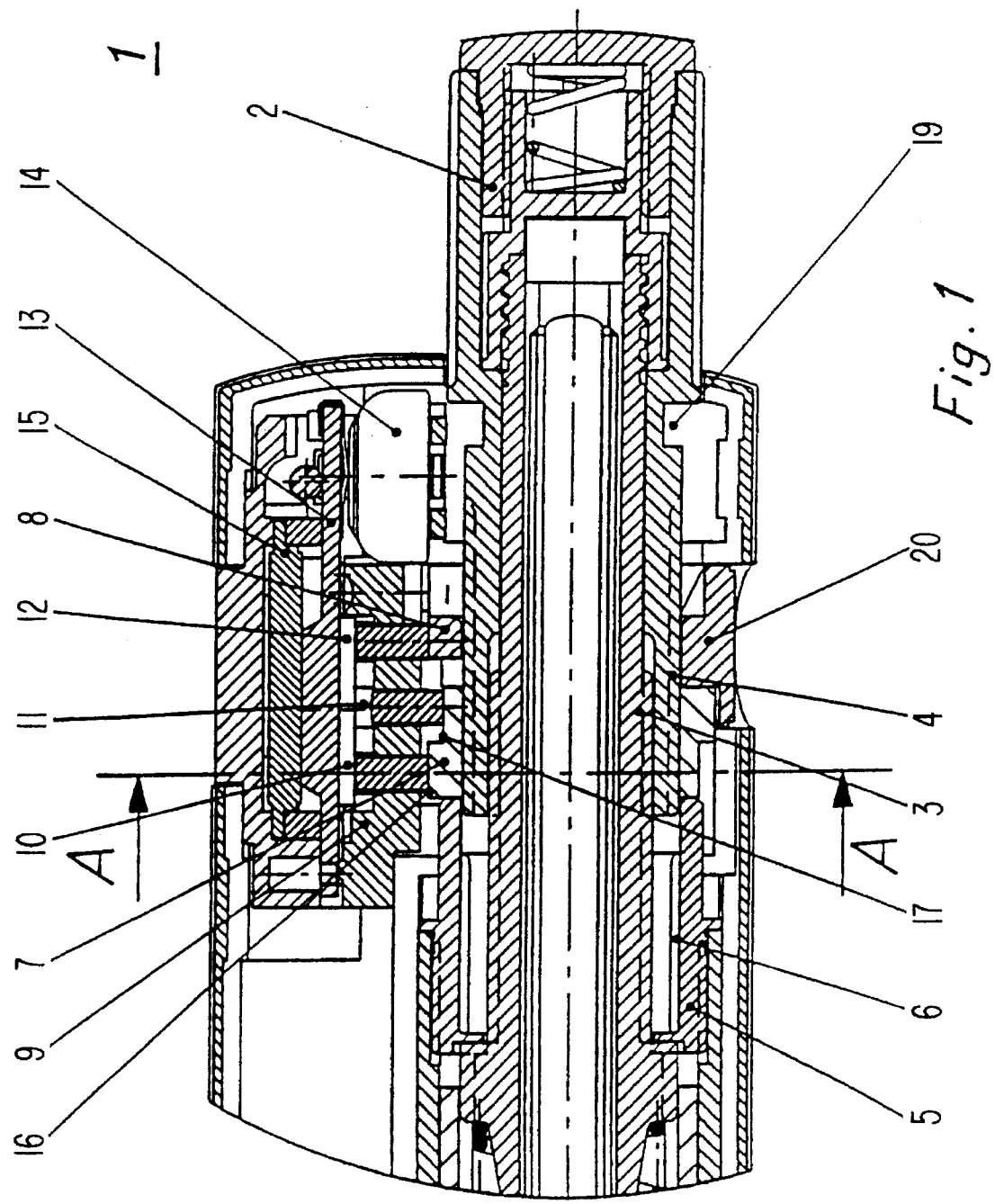
FIG. 1 is a longitudinal section of an injection device with a display of the invention located on the side of the operating head.
Figure 2:
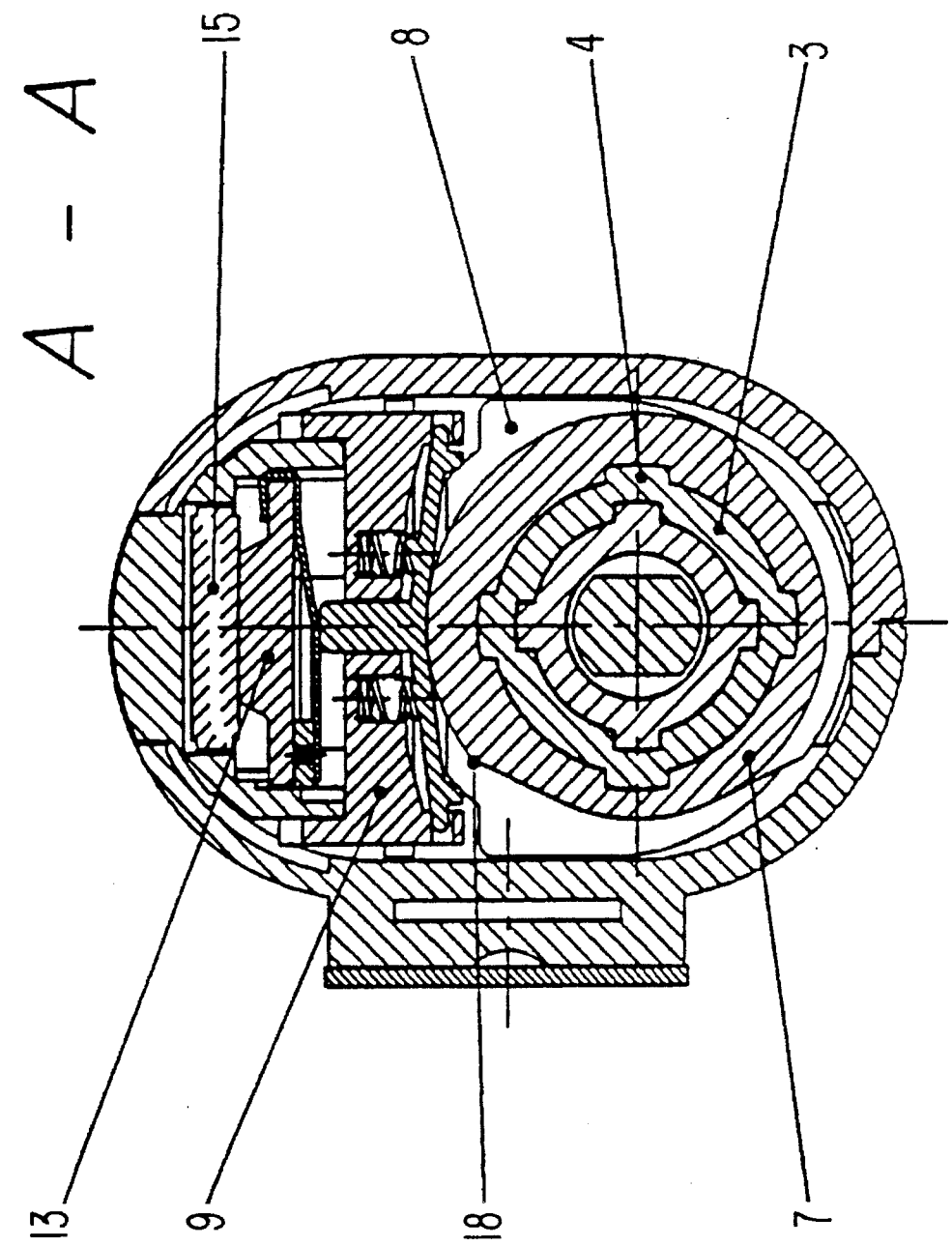
FIG. 2 is a cross-section along line A—A of the device of FIG. 1.

A display according to the invention mounted on an injection device 1 partly shown in FIGS. 1 and 2 and moreover illustratively similar to that of WO 87/02895 comprises an axial operating head 2 with a cylindrical part 3, said head being rotatable in order to set the magnitude of the dose to be thereupon injected and further being slidably movable axially to carry out the injection. The rotations of the operating head 2 are composed of continuous fractional turns of which a given number amounts to one revolution. Illustratively the fractional turns may be quarter-turns.

When, and only when, the rotatable head is in a position of a terminated fractional turn can the operating head 2 can be displaced only axially: the cylindrical part 3 of the operating head 2 has a number of axial lengthwise bosses 4 corresponding to the number of fractional turns and which, upon axial displacement of the operating head 2, engage the same number of longitudinal channels 6 in a housing wall 5 and thereby prevent rotation. The final axial position, that is the position wherein the longitudinal bosses 4 fully engage the longitudinal channels 6, is smitted from the drawing, but their rest positions are shown, namely, in which rotation of the operating head 2 is possible because then there is no engagement between the longitudinal bosses 4 and the longitudinal channels 6. The operating head 2 advanced into the end position is returned into the rest position by elastic means omitted from the drawing but located in the lower part of the device 1.

Switch operation means 7, 8 are apposed to the operating head 2 and can be actuated by its motion. They engage a switch part 9 and in turn actuate switches 10, 11 and 12. Switch part 9 is connected to a printed-circuit board 13 powered by a battery 14 and said board in turn is electrically connected to a display 15 such as an LCD system.

These switch means 7, 8 may form signals as a result of the rotation, in which event they will be called "boss" or "cam" rings 7, or they may form signals by means of the axial displacement, in which case they are called "switch rings" 8. Preferably the cylindrical part 3 of the operating head 2 passes through the switch means 7, 8.

The cam rings 7 rotate together with the operating head 2, being driven for instance by the longitudinal bosses 4 on the cylindrical part 3 of the operating head 2. However, other transmission means may be provided for rotation. Advantageously they comprise an equal number of circumferentially equidistant bosses 18. A cam ring 7 may comprise several cam surfaces 16, 17 adjoining one another at its outer circumference and with axially offset bosses or shoulders 18. If, as shown in the drawing, cam ring 17 comprises a first cam surface 16 and a second cam surface 17, then the former can actuate a first switch 10 and the latter can actuate a second switch 11 in switch part 9. Advantageously the shoulders 18 of a cam surface 16, 17 are designed in such manner that during the rotation of the operating head 2 the switches 10, 11 located in the plane of a shoulder 18 will always be turned ON by means of a first angular excursion and OFF by means of a second angular excursion. As elucidated further below, the switchover implemented by the shoulders 18 of the switches 10, 11 each time entails the setting of the next injection dose and its display.

Other switch means are designed as switch rings 8 which do not take part in the rotation of the operating head 2. They are prevented from doing so for instance by a stop 20 of the switch ring 8 being rigidly mounted in a hole of the housing wall 5. The cylindrical part of the operating head 2 also passes through the switch ring 8.

A third switch 12 of the switch part 9 is kept in a first position by a switch ring 8 during the rest position and during the transition from rest position to the end position, and back, when the operating head 2 is displaced axially. For the omitted axial end position of the operating head 2, switch ring 8 moves the third switch 12 of the switch part 9 into a second position. For that purpose cylindrical part 3 of operating head 2 is illustratively fitted with an annular channel 19 entered by switch ring 8 for the axial end position, whereby it moves third switch 3 into the second position.

The above procedure is implemented for instance in that switch ring 8 is pressed by a spring behind switch 12 into the annular channel 19 and thereby makes room, as a result of which spring-loaded switch 12 is simultaneously reversed from the first: into the second position. Because the end position of the axial displacement takes place only at the end of injection, switch ring 8 allows counting the number of administered injections.

Cam rings 7 and switch rings 8, through switches 10, 11, 12, drive an electric part of the display essentially consisting of a printed-circuit board 13, a battery 14 and an LCD system 15. Printed-circuit board 13 contains a processor receiving its inputs from the switch positions of switches 10, 11, 12 and allowing performance of the following functions, counting the time of display counting the fractional turns when setting an injection dose, counting a "reserve" which is computed from the difference between the volume of injection liquid when the ampoule was inserted minus all the set injection doses up to that time based on the partial rotations, and counting the output of injection doses based on the fractional turns.

Accordingly the number of fractional turns of the operating head 2 to increase the set injection dose is added by the display over the entire capacity range of the liquid receptacle or to enlarge the pre-set dose, or it is subtracted when reversing the direction of rotation.

The count of display duration determines the duration during which one of the above listed magnitudes can be displayed by LCD system 15 unless another magnitude is already displayed. Illustratively, this duration is 128 seconds for the device shown. When setting the injection dose in the illustratively shown device of FIGS. 1 and 2, the fractional turns, which, as mentioned above are quarter-turns of the operating head 2, are counted by means of a cam ring 17 and switch 10, 11 with a 2-position binary counter of the processor, and according to the position of operating head 2, the binary numbers 00, 10, 11, and 01 will be the outputs at LCD system 15.

Again as mentioned above, because the first and second switches 10, 11 actuated by the rotation of operating head 2 and by cam ring 7 and shoulders 18 are reversed shortly before the end of the corresponding fractional turns, operating head 2 can be rotated arbitrarily clockwise or counterclockwise without giving rise to errors in ascertaining its position from the readout of the LCD system. The signals formed are shown in FIG. 3.

Figure 3:
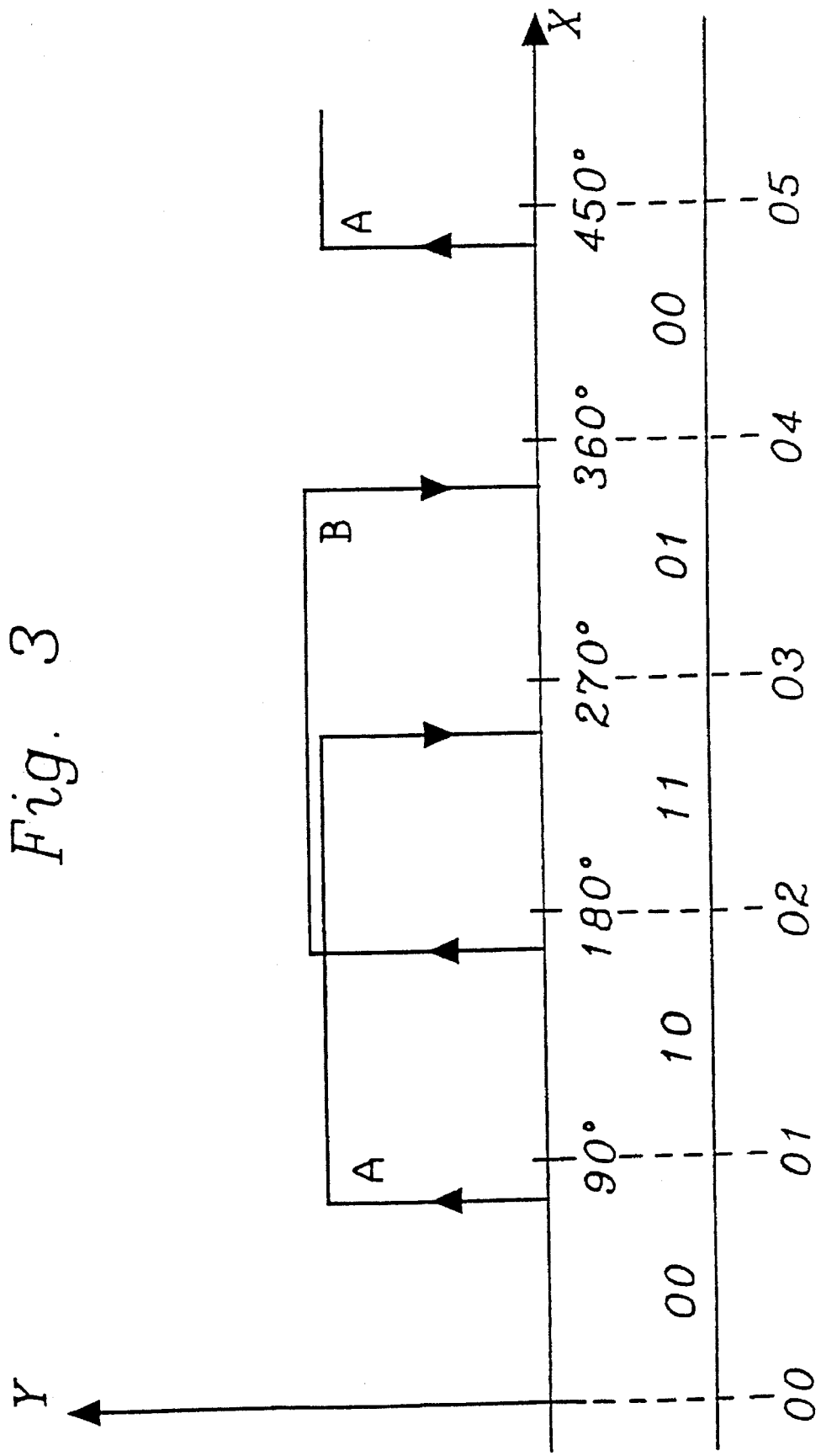
FIG. 3 shows the sequence of signals from the display when the operating head is being rotated.

The x-axis of FIG. 3 shows the angular excursion and the y-axis the signal magnitudes at the display output for setting the injection dose, while the abscissa below shows the associated readout of a binary counter and below that the associated display of an LCD system.

Shortly before the end of the first fractional turn (prior to 90°), first boss 18 of the first cam surface 16 reverses first switch 10 and raises the signal A. Illustratively the binary number 10 appears at the LCD system which in this case is counting in the binary mode.

Shortly before the end of the second fractional turn (prior to 180°) second shoulders 18' of the second cam surface 17 reverses second switch 11 and raises the second signal B. The first signal remains at its previous amplitude. The binary number 11 appears at the LCD system.

Shortly before the end of the third fractional turn (prior to 270°) first shoulder 18 of the first cam surface 16 moves back first switch 10 and moves down the first signal A. The second signal remains high. The binary number 01 appears at the LCD system.

Shortly before the end of the fourth fractional turn (prior to 360°) second shoulder 18' of the second cam surface 17 moves back the second switch and moves down the second signal B. The first signal remains low. The LCD system 15 displays the binary number 00.

This procedure continues to the end of the rotation of operating head 2 after the injection dose has been set. The binary numbers also may be stated in another sequence.

The number of fractional turns moreover is summed by an LCD counter and appears as a decimal number, after the end of the rotation, at the LCD system 15. It indicates the magnitude of the set injection dose based on the number of fractional turns. This display will be erased for the axial end position of operating head 2, that is, after the injection of the set injection dose, by the processor and through switch ring 8 and third switch 12 with the time-delay of the display-duration count.

The number of the injected fractional turns is subtracted from a reserve counter automatically set, upon new-ampoule insertion, to the total injection quantity from this ampoule, based on the number of possible fractional turns. This reserve counter shows a conspicuous special alarm character, for instance a flickering "tt" on LCD system 15 in lieu of the set dose if the set dose exceeds the still extent reserve of injection liquid.

The processor may contain a timer. If the maximum allowed time to administer an injection from the inserted ampoule is exceeded, then a special alarm character such as a flickering "bb" can be displayed at the LCD system 15 after an attempt was made to set an injection dose.

Moreover the processor monitors the battery power output. If the power has become too low, it will display a warning sign such a flickering "bt" at the LCD system 15 after an attempt was made to set an injection dose.

Furthermore discrete circuits with preset functions may be used in lieu of a processor on the printed-circuit board 13 to carry out the above operations. Speaking broadly, one may consider that the said operations can be implemented by the printed-circuit board 13.

Also different and advantageous display means may be used with the device of the invention. Illustratively the display may be integrated into an injection device wherein the injection dose can be set and the injection itself can be carried out using electrical means.

Following setting of the desired dose, the patient is able to check it thereafter in the injection device by means of the display according to the invention and obtains information how much injection liquid remains for further injections. The display of the invention therefore meets its objective.

I claim:

1. An injection device and display for expelling doses of liquid from a liquid-containing ampoule having a plunger therein and for displaying the status of the dosage and remaining liquid comprising the combination of a generally cylindrical housing having a longitudinal axis;

an operating head having an axially extending cylindrical part, said head and cylindrical part being rotatably carried in said housing;

means in said housing and cylindrical part for permitting axial displacement of said cylindrical part relative to said housing only at selected angular positions of said head and cylindrical part to expel a dose of liquid from said ampoule, said cylindrical part being axially movable between a rest position and a fully depressed end position;

a liquid-crystal display on said housing;

first switch means operated by rotation of said head for producing signals representative of rotation of said head to said angular positions and of direction of rotation; second switch means for producing signals representative of axial displacement of said cylindrical part relative to said housing; and printed circuit means having a battery, said printed circuit means being connected to receive said signals from said first and second switch means and to operate said display, said signals from said first switch means in one direction of rotation being added by said printed circuit means and signals in an opposite direction being subtracted to thereby determine a number of doses, and said signals from said second switch means being accumulated to indicate a number of expelled doses.

2. A device according to claim 1 wherein said means for permitting axial displacement comprises a plurality of axially extending bosses on said cylindrical part corresponding in number to a selected number of fractional turns required for a full revolution of said head and cylindrical part, and an equal number of axially extending channels in said housing, said bosses engaging said channels only when said head and cylindrical part are rotated to align said bosses and channels and said cylindrical part is displaced to expel liquid from said ampoule, rotation between said head and said housing being possible only when said bosses and channels are not engaged.

3. A device according to claim 2 wherein said first switch means includes cam rings penetrated by said cylindrical part and rotatable therewith.

4. A device according to claim 3 wherein said cam rings include means defining internal recesses engaging said bosses whereby said cam rings are rotatively driven by said bosses.

5. A device according to claim 1 wherein said first switch means includes cam rings penetrated by said cylindrical part and rotatable therewith.

6. A device according to claim 5 wherein one said cam ring includes means defining axially offset cam surfaces having switch operating shoulders, each for operating one of a plurality of switches.

7. A device according to claim 6 wherein said cam surfaces are shaped so that, during rotation of said head, one said shoulder of a cam surface turns a switch on and another said shoulder of said cam surface turns said switch off.

8. A device according to claim 7 wherein said shoulders are circumferentially positioned so that said switch is turned off shortly before the end of a fractional turn of said head.

9. A device according to claim 1 wherein said second switch means comprise a switch ring non-rotatively penetrated by said cylindrical part and restrained against axial movement.

10. A device according to claim 9 wherein said switch ring holds a switch in a single position when said cylindrical part is between said rest position and said end position, and moves said switch to a second position only in said end position.

11. A device according to claim 10 wherein said cylindrical part includes an annular channel to receive said switch ring in said end position, permitting lateral movement of said switch ring to move said switch to said second position.

* * * * *